June 22, 1965 E. S. BOERNER Plant Pat. 2,541
ROSE PLANT
Filed March 24, 1964
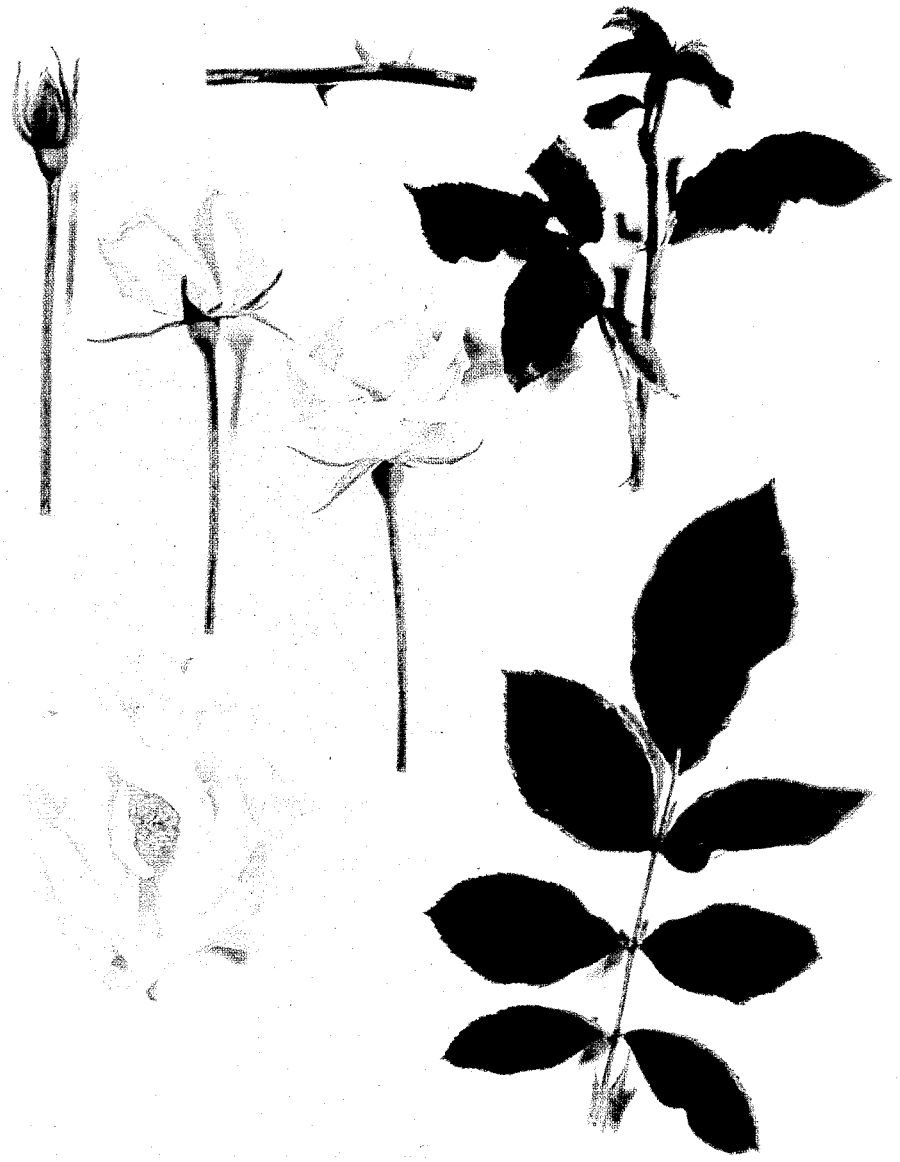
Inventor.
E. S. Boerner
By: Robb & Robb
Attorneys.

United States Patent Office

Plant Pat. 2,541
Patented June 22, 1965

2,541
ROSE PLANT

Eugene S. Boerner, Newark, N.Y., assignor to Jackson & Perkins Company, Newark, N.Y., a corporation of New York Filed Mar. 24, 1964, Ser. No. 354,490
1 Claim. (Cl. Plt.—26)

The present invention relates to a new and distinct variety of rose plant of the floribunda class, which was originated by me by crossing the variety known as "Seventeen" (Plant Patent No. 1,765), with an unnamed and unpatented seedling of "Demure" (Plant Patent No. 1,065).

The primary object of this breeding was to produce a new and improved rose variety in which there is combined a stronger plant habit, with a flower color generally similar to that of the variety "Seventeen." This objective was fully achieved, along with other desirable features, as evidenced by the following unique combination of characteristics which are outstanding in the new variety and which distinguish it from its parents, as well as from all other varieties of which I am aware:

(1) A very vigorous and strong habit of growth;

(2) Exceptionally good flower production, both outdoors and in the greenhouse;

(3) An attractive flower shape and medium flower size;

(4) A distinctive and attractive general color tonality of the flowers corresponding to La France Pink, lightly overcast with Thulite Pink; and (5) Very long-lasting flower qualities, both on the plant and as cut flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawings shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Seventeen."
*Pollen parent.*—Seedling of "Demure."
Classification:
*Botanic.*—Floribunda.
*Commercial.*—Floribunda.

*Flower*

(Observations made from specimens grown in greenhouse at Newark, New York, during the first part of the month of January.)

Blooming habit: Recurrent—continuous.
Bud:
*Size.*—Medium.
*Form.*—Ovoid-pointed; is not affected by wet or hot weather.
*Color.*—When sepals first divide—Tyrian Rose, Plate 12. When petals begin to unfurl—Eugenia Red, Plate 13, very lightly overcast with La France Pink, Plate 1. When half-blown: inside of petals—Venetian Pink, Plate 13, very lightly overcast with Orient Pink, Plate 2 on the outer edge of the petals; reverse of petals—Eosine Pink, Plate 1, very lightly overcast with Thulite Pink, Plate 26.
*Sepals.*—Slightly branched; curl back when petals begin to unfurl. Color: inside — Chromium Green, Plate 32; outside—Spinach Green, Plate 5.
*Calyx.*—Color—Spinach Green, Plate 5. Shape—pear. Size—small. Aspect—smooth. Odor when rubbed—none.
*Peduncle.*—Length—medium. Aspect—prickly. Color—Lettuce Green, Plate 5. Strength—erect; slender.
*Opening.*—Opens up well; is not affected by adverse weather conditions.

Bloom:
*Size.*—Medium. Average size when fully expanded—3½–4 inches.
*Borne.*—Both singly and several together; produces many flowers both in greenhouse and in outdoor gardens.
*Stems.*—Medium length; strong.
*Form (when first open).*—High-centered. Permanence—retains its form to the end.
*Petalage.*—Double (full but open center). Number of petals under normal conditions—from 30 to 35.
*Color.*—Center of flower—La France Pink, Plate 1, overcast with Thulite Pink, Plate 26. Outer petals—Shrimp Pink, Plate 1, lightly overcast with Rose Pink, Plate 12 on the edge of the petals. Base of petals (aiglet)—Pale Dull Green-Yellow, Plate 17. Inside of petals—La France Pink, Plate 1, lightly overcast with Thulite Pink, Plate 26. Reverse of petals—Hermosa Pink, Plate 1. General tonality from a distance—La France Pink, Plate 1, overcast wtih Thulite Pink, Plate 26.
*Discoloration.*—General tonality at end of first day—La France Pink, Plate 1, overcast with Thulite Pink, Plate 26. Second day—La France Pink, Plate 1, overcast with Thulite Pink, Plate 26. Third day—La France Pink, Plate 1, lightly overcast with Thulite Pink, Plate 26.

Petals:
*Texture.*—Leathery; is not affected by wet or hot weather.
*Appearance.*—Inside—satiny. Outside—shiny.
*Form.*—Oval; slightly notched.
*Arrangement.*—Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On plant—very long. As cut flower—very long.

*Genital organs*

Stamens, anthers: Medium size; many; regularly arranged around styles. Color—Buff-Yellow, Plate 4.
Stamens, filament (threads): Medium length. Color—Picric Yellow, Plate 4.
Pollen: Color—Maize Yellow, Plate 4.
Styles: Bunched; uneven length; medium length; thin.
Stigmas: Color—Chartreuse Yellow, Plate 31.
Ovaries: All enclosed in calyx.
Hips: None.
Seeds: None.

*Plant*

Form: Bush.
Growth: Very vigorous and strong; branching.
Foliage: Compound of 5–7 leaflets.
*Size.*—Large.
*Quantity.*—Normal.
*Color.*—New foliage: upper side—Varley's Green, Plate 18, overcast with Hay's Maroon, Plate 13;

under side—Indian Lake, Plate 26. Old foliage: upper side—Forest Green, Plate 17; under side—Courge Green, Plate 17.

*Shape.*—Oval pointed.

*Texture.*—Upper side—glossy. Under side—smooth.

*Ribs and veins.*—Ordinary.

*Edge.*—Serrated (saw toothed).

*Serration.*—Both double and single; small.

*Leaf stem.*—Color—Light Bice Green, Plate 17. Under side—rough.

*Stipules.*—Medium length; smooth.

Wood:

*New wood.*—Color—Parrot Green, Plate 6, lightly overcast with Oxblood Red, Plate 1. Bark—smooth.

*Old wood.*—Color—Elm Green, Plate 17. Bark—smooth.

Thorns:

*Thorns.*—Quantity: on main stalks from base—many; on laterals from stalk—ordinary. Form—flat base; medium length; hooked downward.

Color (when young)—Begonia Rose, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of a very vigorous and strong habit of growth, exceptionally good flower production, both outdoors and in the greenhouse, an attractive flower shape and medium flower size, a distinctive and attractive general color tonality of the flowers corresponding to La France Pink, lightly overcast with Thulite Pink, and very long-lasting flower qualities, both on the plant and as cut flowers.

No references cited.

ABRAHAM G. STONE, *Primary Examiner.*